United States Patent
Qiu et al.

(10) Patent No.: US 7,786,330 B2
(45) Date of Patent: Aug. 31, 2010

(54) PROCESS FOR PRODUCING 1,2-DIALKOXY-3-FLUOROBENZENE

(75) Inventors: Mingjian Qiu, Beijing (CN); Wei Zhang, Beijing (CN); Zhaohui Chen, Beijing (CN); Chunshan Zhang, Beijing (CN); Yali Zhang, Beijing (CN)

(73) Assignees: Asahi Glass Company, Limited, Tokyo (JP); Charna Chemicals, Ltd., Beijing (CN)

( * ) Notice: Subject to any disclaimer, the term of this patent is extended or adjusted under 35 U.S.C. 154(b) by 0 days.

(21) Appl. No.: 12/379,553

(22) Filed: Feb. 24, 2009

(65) Prior Publication Data

US 2009/0227817 A1    Sep. 10, 2009

Related U.S. Application Data

(63) Continuation of application No. PCT/JP2006/316753, filed on Aug. 25, 2006.

(30) Foreign Application Priority Data

Feb. 28, 2005    (CN)    ......................... 200510008983

(51) Int. Cl.
*C07C 37/04*    (2006.01)
*C07C 41/26*    (2006.01)
(52) U.S. Cl. .................. 568/795; 568/629; 568/649; 568/656
(58) Field of Classification Search .................. None
See application file for complete search history.

(56) References Cited

U.S. PATENT DOCUMENTS

| | | | |
|---|---|---|---|
| 4,550,192 A | | 10/1985 | Rogers et al. |
| 4,634,705 A | * | 1/1987 | DeBernardis et al. ....... 514/256 |
| 4,725,683 A | * | 2/1988 | Rogers et al. ............... 544/162 |
| 5,968,856 A | | 10/1999 | Schweiger et al. |
| 5,968,865 A | | 10/1999 | Wilson et al. |
| 6,124,507 A | | 9/2000 | Wilson et al. |
| 6,399,837 B1 | | 6/2002 | Wilson et al. |
| 2005/0004204 A1 | | 1/2005 | Suzuki et al. |
| 2006/0058370 A1 | | 3/2006 | Shimomura et al. |
| 2008/0214834 A1 | | 9/2008 | Yoshizawa et al. |

FOREIGN PATENT DOCUMENTS

| | | |
|---|---|---|
| JP | 60-166638 A | 8/1985 |
| JP | 2005-314322 | 11/2005 |
| JP | 2005-314322 A | 11/2005 |
| WO | WO 02/085855 | 10/2002 |
| WO | WO 03/039599 A1 | 5/2003 |
| WO | WO 2004/078721 | 9/2004 |
| WO | WO 2006/018955 | 2/2006 |

OTHER PUBLICATIONS

Gershon et al., Monatshefte Für Chemie Chemical Monthly, 1999, vol. 130 p. 653-659.*
Gershon et al., 130 Monatshefte Für Chemie, 653-59 (1999).*
Herman Gershon, Preparation and Fungitoxicity of Some Dichloro-8-Quinolinols, Monatshefte fur Chemie Chemical Monthly, 1999, vol. 130 p. 653-659, Scheme 1, 2, Austria.
Supplementary European Search Report issued Jun. 8, 2010, for European Patent Application 06783042.2, 5 pgs.
Database WPI Week 200708 Thomson Scientific, London, Great Britain, AN 2007-073924 XP-002581545 & CN 1 740 130 A (Dalian Luyuan Phar Mind Co Ltd) Mar. 1, 2006, retrieved on May 11, 2010, 1 pg.

* cited by examiner

*Primary Examiner*—Brian J Davis
(74) *Attorney, Agent, or Firm*—Foley & Lardner LLP

(57) ABSTRACT

The present invention relates to a process for producing a 2-fluoro-6-halophenol as an intermediate; a process for producing a 2-alkoxy-3-fluorophenol and further a 1,2-dialkoxy-3-fluorobenzene from the 2-fluoro-6-halophenol; a second process for producing a 1,2-dialkoxy-3-fluorobenzene from the 2-fluoro-6-halophenol; and a 2-alkoxy-3-fluorophenol. The 2-fluoro-6-halophenol can be obtained using a 2-fluorophenol as a starting material and through a sulfonation reaction, a halogenation reaction, and a deprotection reaction. The 2-fluoro-6-halophenol is alkyl-etherified, and subsequently the halogen atom is converted into a hydroxyl group to obtain the 2-alkoxy-3-fluorophenol, which is further alkyl-etherified to thereby obtain the 1,2-dialkoxy-3-fluorobenzene. Alternatively, a 1,2-dialkoxy-3-fluorobenzene is also obtained by converting the halogen atom of the 2-fluoro-6-halophenol into a hydroxyl group to thereby form 3-fluorocatechol and subsequently alkyl-etherifying two hydroxyl groups thereof. The processes of the invention realize low production costs and high process yields, and thus are suitable for industrial production of a 1,2-dialkoxy-3-fluorobenzene.

10 Claims, No Drawings

PROCESS FOR PRODUCING 1,2-DIALKOXY-3-FLUOROBENZENE

TECHNICAL FIELD

The present invention relates to a process for producing a 1,2-dialkoxy-3-fluorobenzene using 2-fluorobenzene as a starting material and through a 2-fluoro-6-halophenol as an intermediate. The 1,2-dialkoxy-3-fluorobenzene is a useful compound as a medicament intermediate or the like.

BACKGROUND ART

Dialkoxybenzene-based compounds have widely been utilized as extremely strong electron donors in many fields and, for example, have been used as intermediates for medicament production, materials for electroluminescence displays and monomers for electrolytic polymerization and also used for production of Ziegler-Natta catalysts for orientation of polyolefins. In particular, 1,2-dialkoxy-3-fluorobenzenes such as 1,2-diethoxy-3-fluorobenzene are known to be useful as intermediates for medicament production (see WO 02/085855, WO 2004/078721, WO 2006/018955). Processes for synthesizing such compounds have been disclosed in U.S. Pat. No. 5,968,865, U.S. Pat. No. 6,124,507, U.S. Pat. No. 6,399,837 and WO 02/085855. However, in the processes described therein, 2-alkoxyphenol-based compounds are used as starting materials and are reacted with alkyl halides under a strong alkaline atmosphere to introduce other alkoxy groups. In such synthetic processes, the costs of the starting materials are high, the process yields are low, a large amount of sodium hydroxide is required, and also excess alkyl halides are generated in a large amount, so that a post-treatment step becomes troublesome. Therefore, the processes are not suitable for industrial production. Furthermore, there is known a process using 3-fluoroanisole as a starting material and through a (2-alkoxy-6-fluorophenyl) borate derivative (see JP-A-2005-314322).

DISCLOSURE OF THE INVENTION

Problems to be Solved by the Invention

An object of the invention is to produce a 1,2-dialkoxy-3-fluorobenzene in a high process yield and a low production cost.

Means for Solving the Problems

The invention relates to a process for producing a 1,2-dialkoxy-3-fluorobenzene using 2-fluorophenol as a starting material and through a 2-fluoro-6-halophenol; a process for producing the 2-fluoro-6-halophenol as an intermediate; a process for producing a 2-alkoxy-3-fluorophenol as an intermediate substance in the production of a 1,2-dialkoxy-3-fluorobenzene from a 2-fluoro-6-halophenol; and 2-ethoxy-3-fluorophenol as a representative compound of the 2-alkoxy-3-fluorophenol.

[1] A process for producing a 2-fluoro-6-halophenol, which comprises producing a 2-fluoro-6-halophenol (provided that the halogen atom at the 6-position is a halogen atom other than a fluorine atom), using 2-fluorophenol as a starting material, by performing the following steps in the described order:

(1) a sulfonation reaction step of introducing a sulfonic acid group into the 4-position with a sulfonating reagent;

(2) a halogenation reaction step of introducing a halogen atom into the 6-position using a halogenating reagent; and (3) a step of carrying out an elimination reaction of the sulfonic acid group in an acidic atmosphere to obtain a 2-fluoro-6-halophenol.

[2] A process for producing a 2-alkoxy-3-fluorophenol, which comprises producing a 2-alkoxy-3-fluorophenol (provided that the alkoxy group has 20 or less carbon atoms), using 2-fluorophenol as a starting material, by performing the following steps in the described order:

(1) a sulfonation reaction step of introducing a sulfonic acid group into the 4-position with a sulfonating reagent;

(2) a halogenation reaction step of introducing a halogen atom (provided that the halogen atom is a halogen atom other than a fluorine atom) into the 6-position using a halogenating reagent;

(3) a step of carrying out an elimination reaction of the sulfonic acid group in an acidic atmosphere to obtain a 2-fluoro-6-halophenol;

(4) an etherification reaction step of alkyl-etherifying the hydroxyl group with an alkylating reagent to obtain a 1-alkoxy-2-fluoro-6-halobenzene; and (5) a hydroxylation reaction step of converting the halogen atom into a hydroxyl group by a hydrolysis reaction or a Grignard reaction to obtain a 2-alkoxy-3-fluorophenol.

[3] The process according to the above (2), wherein the alkoxy group is an ethoxy group.

[4] A process for producing a 1,2-dialkoxy-3-fluorobenzene, which comprises producing a 1,2-dialkoxy-3-fluorobenzene (provided that the two alkoxy groups are the same or different alkoxy groups and both are alkoxy groups having 20 or less carbon atoms), using 2-fluorophenol as a starting material, by performing the following steps in the described order:

(1) a sulfonation reaction step of introducing a sulfonic acid group into the 4-position with a sulfonating reagent;

(2) a halogenation reaction step of introducing a halogen atom (provided that the halogen atom is a halogen atom other than a fluorine atom) into the 6-position using a halogenating reagent;

(3) a step of carrying out an elimination reaction of the sulfonic acid group in an acidic atmosphere to obtain a 2-fluoro-6-halophenol;

(4) an etherification reaction step of alkyl-etherifying the hydroxyl group with an alkylating reagent to obtain a 1-alkoxy-2-fluoro-6-halobenzene;

(5) a hydroxylation reaction step of converting the halogen atom into a hydroxyl group by a hydrolysis reaction or a Grignard reaction to obtain a 2-alkoxy-3-fluorophenol; and (6) an etherification reaction step of alkyl-etherifying the hydroxyl group with an alkylating reagent to obtain a 1,2-dialkoxy-3-fluorobenzene.

[5] The process according to the above [4], wherein both of the two alkoxy groups are ethoxy groups.

[6] A process for producing a 1,2-dialkoxy-3-fluorobenzene, which comprises producing a 1,2-dialkoxy-3-fluorobenzene (provided that the two alkoxy groups are the same or different alkoxy groups and both are alkoxy groups having 20 or less carbon atoms), using 2-fluorophenol as a starting material, by performing the following steps in the described order:

(1) a sulfonation reaction, step of introducing a sulfonic acid group into the 4-position with a sulfonating reagent;

(2) a halogenation reaction step of introducing a halogen atom (provided that the halogen atom is a halogen atom other than a fluorine atom) into the 6-position using a halogenating reagent;

(3) a step of carrying out an elimination reaction of the sulfonic acid group in an acidic atmosphere to obtain a 2-fluoro-6-halophenol;

(7) a hydroxylation reaction step of converting the halogen atom into a hydroxyl group by a hydrolysis reaction or a Grignard reaction to obtain 3-fluorocatechol; and (8) an etherification reaction step of alkyl-etherifying the two hydroxyl groups with an alkylating reagent to obtain a 1,2-dialkoxy-3-fluorobenzene.

[7] The process according to the above [6], wherein both of the two alkoxy groups are ethoxy groups.

[8] The process according to any of the above [1] to [7], wherein the sulfonating reagent is concentrated sulfuric acid, fuming sulfuric acid, chlorosulfonic acid, or a molecular composite of anhydrous pyridine with sulfur trioxide.

[9] The process according to any of the above [1] to [8], wherein the halogenating reagent is $Cl_2$, $Br_2$, $I_2$, or ICl.

[10] 2-Ethoxy-3-fluorophenol.

ADVANTAGEOUS EFFECT OF THE INVENTION

According to the process of the invention, it is easy to obtain starting materials. Moreover, since a halogen atom is introduced into the 6-position after the 4-position is protected by a sulfonation reaction, a highly pure 2-fluoro-6-halophenol can be obtained without performing complex separation and purification steps as compared with the process of carrying out a direct halogenation reaction without protecting the 4-position. Namely, in the process of carrying out a direct halogenation reaction, there arises a problem that hydrogen atoms at the 4- and 6-positions are replaced with halogen atoms at the same time to form two kinds of isomers (a compound halogenated at the 4-position and a compound halogenated at the 6-position) which are difficult to separate. However, this problem can be avoided in the process of the invention. Furthermore, since all of the sulfonation reaction, the halogenation reaction, and the deprotection reaction are easy to realize, the production costs are remarkably reduced. According to the invention, since two phenolic hydroxyl groups can be separately alkylated in the production of the 1,2-dialkoxy-3-fluorobenzene, even in the case of producing a 1,2-dialkoxy-3-fluorobenzene having different alkoxy groups at the 1- and 2-positions, it can be easily obtained. The production process of the invention has many steps, but the steps are each easy to realize and the process does not require any difficult reaction conditions and the process yields are high, so that the process is extremely suitable for industrial production.

BEST MODE FOR CARRYING OUT THE INVENTION

Respective compounds in the invention are those represented by the following structural formulae.

[Chem.1]

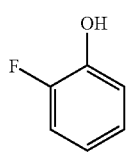
[A]

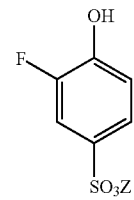
[B]

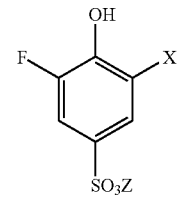
[C]

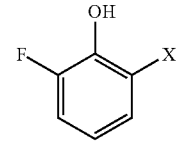
[D]

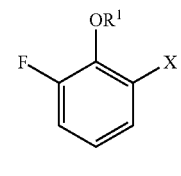
[E]

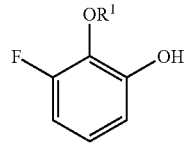
[F]

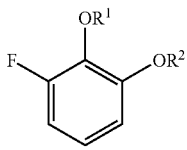
[G]

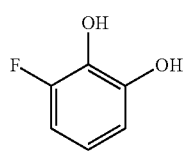
[H]

In the structural formulae, Z represents a hydrogen atom or a monovalent cation. The monovalent cation is preferably an alkali metal cation, particularly preferably a sodium ion. X represents a halogen atom other than a fluorine atom, i.e., a chlorine atom, a bromine atom or an iodine atom. In the following explanation of the invention, halogen means halogens other than fluorine unless otherwise stated. X is preferably a bromine atom or an iodine atom, particularly preferably a bromine atom.

$R^1$ and $R^2$ each independently represent an alkyl group having 20 or less carbon atoms. The alkyl group may be either a linear alkyl group or a branched alkyl group. As the alkyl group, an alkyl group having 1 to 6 carbon atom is preferred. Specific examples of the alkyl groups include, for example, a methyl group, an ethyl group, an n-propyl group, an isopropyl group, an n-butyl group, a t-butyl group, an n-pentyl group, a 3-methylbutyl group, an n-hexyl group, a 3-methylpentyl group, a 4-methylpentyl group, a 3,3-dimethyl group and the like. It is preferred that at least one of $R^1$ and $R^2$ is an ethyl group (the other one is an alkyl group having 1 to 6 carbon atoms), and it is particularly preferred that both are ethyl groups.

The steps are each described below. The symbols A to H attached to the end of compound names correspond to the symbols indicated with the foregoing structural formulae.

Step (1): a step of reacting 2-fluorophenol [A] with a sulfonating reagent to produce a compound [B] having a sulfonic acid group ($SO_3Z$) at the 4-position.

The sulfonating reagent includes, for example, concentrated sulfuric acid, fuming sulfuric acid, chlorosulfonic acid and a molecular composite of anhydrous pyridine with sulfur trioxide. Particularly, concentrated sulfuric acid is preferred. Using the sulfonating reagent, 2-fluorophenol [A] is treated under a temperature of 50 to 150° C., preferably under a temperature of 100 to 120° C. for 1 to 10 hours, preferably 4 to 6 hours to introduce —$SO_3H$ into the 4-position. The sulfonation reaction is preferably carried out at a temperature of 50 to 150° C. for 1 to 10 hours.

After the introduction of —$SO_3H$, it is preferred to convert the hydrogen atom of the —$SO_3H$ group into a cation by the treatment with a cation source. As the cation, an alkali metal cation is preferred and sodium ion is particularly preferred. Thereby, interference by the hydrogen atom of the —$SO_3H$ group can be avoided in the next halogenation reaction. Specifically, after the sulfonation reaction, sodium salt of the sulfonated compound can be precipitated by the treatment with an aqueous sodium hydroxide solution, a saturated aqueous sodium chloride solution, an aqueous solution of a basic sodium salt such as sodium carbonate or sodium hydrogen carbonate, or the like, Step (2): a step of reacting the compound [B] with a halogenating reagent to introduce a halogen atom into the 6-position of the compound [B], thereby a compound [C] having a sulfonic acid group ($SO_3Z$) at the 4-position and a halogen atom (X) at the 6-position.

The halogenating reagent includes, for example, $Cl_2$, $Br_2$, $I_2$, ICl and the like. The above compound [B] is treated with a halogenating reagent under a temperature of 30 to 100° C., preferably under a temperature of 50 to 80° C. for 1 to 10 hours, preferably 3 to 5 hours to introduce a halogen atom X into the 6-position, thereby the compound [C] being produced. The halogenation reaction is preferably carried out under a temperature of 30 to 100° C. for 1 to 10 hours. The reaction can be carried out in a solvent. The solvent include, for example, halogenated hydrocarbons such as dichloromethane, trichloromethane, carbon tetrachloride and dichloroethane.

Step (3): a step of subjecting the compound [C] to an elimination reaction of a sulfonic acid group ($SO_3Z$) in an acidic atmosphere to convert the sulfonic acid group at the 4-position into a hydrogen atom, thereby 2-fluoro-6-halophenol [D] being produced.

The step (3) relates to a deprotection reaction of converting the sulfonic acid group ($SO_3Z$) as a protective group which has protected the 4-position of the compound [C] into a hydrogen atom. The reaction is carried out by heating the compound [C] in an acidic atmosphere. It is preferred that the deprotection reaction is carried out under a temperature of 100 to 200° C., preferably under a temperature of 150 to 180° C. The reaction time is 1 to 10 hours, preferably 3 to 6 hours. The deprotection reaction is preferably carried out under a temperature of 100 to 200° C. for 1 to 10 hours. In order to carry out the reaction in an acidic atmosphere, the reaction is preferably carried out in the presence of an acid, and the reaction is particularly preferably carried out in an aqueous acid solution having a high concentration. The acid includes inorganic acids such as sulfuric acid, hydrochloric acid, nitric acid and phosphoric acid and organic acids such as acetic acid and propionic acid. In particular, the reaction is preferably carried out in an aqueous sulfuric acid solution having a high concentration.

By performing the foregoing steps (1) to (3) successively, 2-fluoro-6-halophenol [D] is obtained from 2-fluorophenol [A]. Further, 2-alkoxy-3-fluorophenol [F] is obtained by performing the following steps (4) and (5) successively.

Step (4): a step of alkyl-etherifying the hydroxyl group of 2-fluoro-6-halophenol [D] with an alkylating reagent to obtain a 1-alkoxy-2-fluoro-6-halobenzene [E].

The etherification reaction of converting the hydroxyl group into an alkoxy group is carried out by reacting the 2-fluoro-6-halophenol [D] with an alkylating reagent. The reaction is preferably carried out in a solvent in an alkaline atmosphere.

The alkylating reagent is an alkylating reagent having the above-mentioned $R^1$ group, and an alkyl halide represented by $R^1X'$ or an alkyl ester represented by $(R^1)_nY$ is preferred. X' represents a halogen atom (a chlorine atom, a bromine atom or an iodine atom), n represents an integer of 1 to 3, and Y represents an n-valent ester group, X' is preferably a chlorine atom or a bromine atom, particularly a bromine atom. Specific examples of the ester group include ester groups such as a carbonate group, a sulfate group, an acetate group, a phosphate group and a nitrate group. n is preferably 2 and the ester group is preferably a sulfate group. Specific examples of the alkylating reagent include bromomethane and dimethyl sulfate in the case where $R^1$ is a methyl group and bromoethane and diethyl sulfate in the case where $R^1$ is an ethyl group.

As a basic substance for making the reaction system alkaline, an alkali metal compound or an alkaline earth metal compound is preferred and a hydroxide or alkoxide of the metal is particularly preferred. For example, the metal hydroxide includes sodium hydroxide, potassium hydroxide, calcium hydroxide and the like. For example, the metal alkoxide includes sodium methoxide, potassium methoxide, sodium ethoxide, potassium ethoxide, sodium isopropoxide, potassium tert-butoxide and the like. As the basic substance, sodium hydroxide and potassium hydroxide are particularly preferred. As the solvent, water and various organic solvents can be employed. As the solvent, alcohols such as methanol and ethanol are preferred and ethanol is particularly preferred.

The alkyl-etherification reaction is preferably carried out by reacting a 2-fluoro-6-halophenol [D] with an alkylating reagent under a reflux temperature of the solvent for 1 to 10 hours, preferably 2 to 5 hours. In particular, as mentioned above, they are preferably reacted in a solvent in an alkaline atmosphere under a reflux temperature of the solvent for 1 to 10 hours.

Step (5); a step of converting the halogen atom of the 1-alkoxy-2-fluoro-6-halobenzene [E] into a hydroxyl group by a hydrolysis reaction or Grignard reaction to obtain a 2-alkoxy-3-fluorophenol [F].

By a hydrolysis method or a method using a Grignard reagent, the halogen atom of the 1-alkoxy-2-fluoro-6-halobenzene [E] is converted into a hydroxyl group by a hydrolysis reaction or a Grignard reaction. In the reaction, a known method frequently used for converting a halogen atom on an aromatic ring into a phenolic hydroxyl group can be employed. For example, the compound [E] is reacted with a base such as an alkali metal hydroxide to effect hydrolysis, whereby the halogen atom can be converted into a hydroxyl group. Moreover, the compound [E] is reacted with magnesium to form a Grignard reagent, and the Grignard reagent is reacted with an oxidizing agent such as an alkyl perbenzoate, alkyl hydroperoxide or oxygen, thereby finally attaining conversion to a hydroxyl group. For example, the Grignard reagent is reacted with N,N-dimethylformamide (DMF) to form an aldehyde group, which may be then reacted with hydrogen peroxide to convert the aldehyde group into a hydroxyl group. Moreover, the Grignard reagent is reacted with an alkyl perbenzoate to form an alkoxy group and then the alkoxy group can be converted into a hydroxyl group. The alkyl group (hereinafter referred to as $R^3$) in the alkyl perbenzoate is usually limited to specific groups (tert-butyl group etc.) owing to the reactivity and hence is not coincident with the objective $R^2$ mentioned below in many cases. Therefore, the alkoxy group ($-OR^3$) obtained by the reaction with the alkyl perbenzoate is then preferably converted into a hydroxyl group. Moreover, in the conversion of the alkoxy group into the hydroxyl group, there arises the necessity of selecting the alkyl group ($R^3$) so that the alkoxy group ($-OR^1$) of the compound [E] is not affected. In the case where $R^1$ of the alkoxy group ($-OR^1$) of the compound [E] is a primary alkyl group, the alkyl group ($R^3$) is preferably a tertiary alkyl group. For the conversion of the alkoxy group ($-OR^3$) into the hydroxyl group, a brønsted acid such as p-toluenesulfonic acid, hydrobromic acid, hydrochloric acid, sulfuric acid, trifluoroacetic acid or acetic acid, or a Lewis acid such as aluminum chloride, boron tribromide, a boron trifluoride-diethyl ether complex is employed.

The reaction of the step (5) is preferably carried out by a method of using a Grignard reagent and, particularly, it is preferred that the halogen atom is converted into a tert-butoxy group by reacting the Grignard reagent with tert-butyl perbenzoate and then the tert-butoxy group is converted into a hydroxyl group. In the case where the halogen atom is an iodine atom, a hydrolysis method can be adopted but in the case where the halogen atom is a bromine atom, there arises a concern that the fluorine atom is also hydrolyzed at the time of hydrolysis. In consideration of the economical efficiency of the whole process of the invention, the halogen atom is preferably a bromine atom, and hence the reaction of the step (5) is preferably carried out by the method of using the Grignard reagent.

By performing the foregoing steps (1) to (5) successively, a 2-alkoxy-3-fluorophenol [F] is obtained from 2-fluorophenol [A]. Furthermore, a 1,2-dialkoxy-3-fluorobenzene [G] is obtained by performing the following step (6).

Step (6): a step of alkyl-etherifying the hydroxyl group of the 2-alkoxy-3-fluorophenol [F] with an alkylating reagent to obtain a 1,2-dialkoxy-3-fluorobenzene [G].

The reaction of the step (6) can be carried out by the method substantially the same as the alkyl-etherification in the above-mentioned step (4). Using an alkylating reagent having an alkyl group $R^2$ as the alkylating reagent, the hydroxyl group of the compound [F] can be converted into an alkoxy group ($-OR^2$). In this connection, although it is usually difficult to assign different alkyl groups to $R^1$ and $R^2$ by the alternative method of producing the 1,2-dialkoxy-3-fluorobenzene [G] described below, this method which is through the step (6) can easily assign different alkyl groups to $R^1$ and $R^2$.

The 1,2-dialkoxy-3-fluorobenzene [G] can be also produced from the 2-fluoro-6-halophenol [D] obtained by performing the foregoing steps (1) to (3) successively, by further performing the following steps (7) and (8) successively.

Step (7): a step of converting the halogen atom of the 2-fluoro-6-halophenol [D] into a hydroxyl group by a hydrolysis reaction or Grignard reaction to obtain a 3-fluorocatechol [H].

The reaction of the step (7) can be carried out in the same manner as in the above-mentioned step (5). However, since it is usually difficult to carry out the reaction of the step (7) by the method using a Grignard reagent, it is preferred to carry out the reaction by a hydrolysis method. The reason why it is difficult to carry out a Grignard reaction is that since the compound [D] has a hydroxyl group, a magnesium salt is apt to form when magnesium is reacted with the compound [D], and thus it becomes difficult to obtain a Grignard reagent. Moreover, since there is a concern that hydrolysis of a fluorine atom may occur in the hydrolysis method as mentioned above, the halogen atom of the 2-fluoro-6-halophenol [D] is preferably an iodine atom in the case of this method which is through the step (7).

Step (8): a step of alkyl-etherifying the two hydroxyl groups of 3-fluorocatechol [H] with an alkylating reagent to obtain a 1,2-dialkoxy-3-fluorobenzene [G].

The reaction of the step (8) can be carried out by the method substantially the same as the alkyl-etherification in the above-mentioned step (4). Using an alkylating reagent, the two hydroxyl groups of the compound [H] can be converted into respective alkoxy groups ($-OR^1$ and $-OR^2$). In this case, $R^1$ and $R^2$ in the compound [G] usually are the same alkyl group.

Next, the present invention will be illustrated in detail based on the following examples. The present invention should not be construed as being limited to these examples.

Example 1

Synthesis of 2-fluoro-6-bromophenol

[Chem. 2]

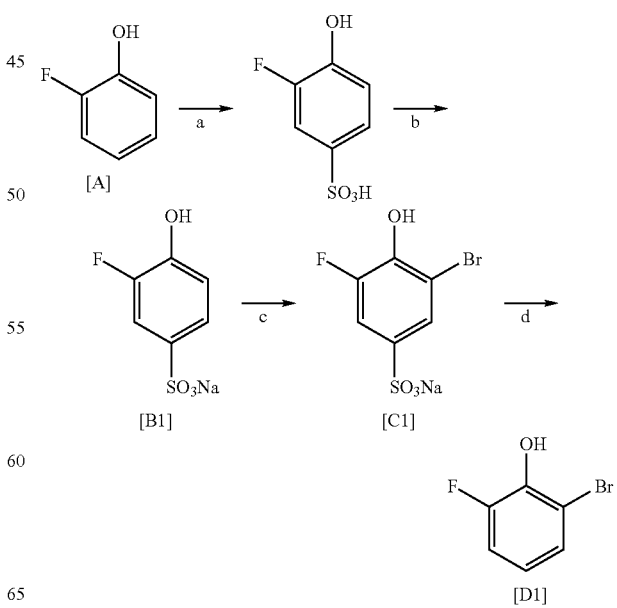

1) Synthesis of sodium 3-fluoro-4-hydroxybenzenesulfonate [B1] (Steps a and b)

a: After 112 g (1.0 mol) of 2-fluorophenol [A] was added to a reactor and heated to around 120° C., 80 ml (1.5 ml) of 98% sulfuric acid was slowly added dropwise over a period of 30 minutes under stirring and, after the termination of the dropwise addition, they were reacted under a temperature of 120° C. for 5 hours. After the termination of the reaction, the mixture was cooled to 100° C. or lower.

b: A saturated sodium chloride solution was added to the above reaction mixture in an amount of 400 ml to precipitate a large amount of the sodium salt. After complete cooling, filtration was performed and washing was conducted twice with a 10% sodium chloride solution to obtain 192.6 g of a product [1,1]. The process yield was 90%.

2) Synthesis of sodium 3-fluoro-6-bromo-4-hydroxybenzenesulfonate [C1] (Step c)

c: Prior to a reaction, all the starting materials and equipments were subjected to anhydrous treatment and bromine was washed twice with concentrated sulfuric acid and then dehydrated. A 250 ml three-necked flask equipped with a mechanical mixer, a thermometer, a liquid-separating funnel and a reflux condenser was used. To the flask were added 171.2 g (0.8 mmol) of [B1], 11.2 g of an iron powder, and 120 ml of carbon tetrachloride. The mixture was heated to 55° C. under stirring on a water bath. While the temperature was kept at 50 to 60° C., 134.4 g (0.84 mol) of bromine was added dropwise over a period of 4 hours. After the dropwise addition, the mixture was stirred for 2 hours while the temperature was kept. After cooling, filtration was performed, the filtrate was washed with water, an alkali water and water in the described order, and the solvent was removed by distillation after drying to obtain 199 g of a product [C1]. The process yield was 85%.

3) Synthesis of 2-fluoro-6-bromophenol [D1] (Step d)

d: To a 250 ml reactor were 146.5 g (0.5 mol) of [C1] and 200 ml of a 70% sulfuric acid solution. They were reacted under a temperature of 180° C. for 5 hours and then cooled to ordinary temperature. Then, 200 ml of dichloromethane was added and extraction was conducted. The extraction liquid was washed and dried and the solvent was removed by distillation to obtain 76.4 g of an oily product [D1]. The process yield was 80%.

Example 2

Synthesis of 2-fluoro-6-iodophenol

Sodium 3-fluoro-6-iodo-4-hydroxybenzenesulfonate was obtained through synthesis by the same reaction process as in Example 1 except that 100 ml of a carbon tetrachloride solution of 213.4 g (0.84 mol) of iodine was used instead of bromine in the step c of Example 1. The process yield was 79%. 2-Fluoro-6-iodophenol was obtained through the deprotection reaction in the step d. The process yield was 83%.

Example 3

Synthesis of 1,2-diethoxy-3-fluorobenzene [G1]

[Chem. 3]

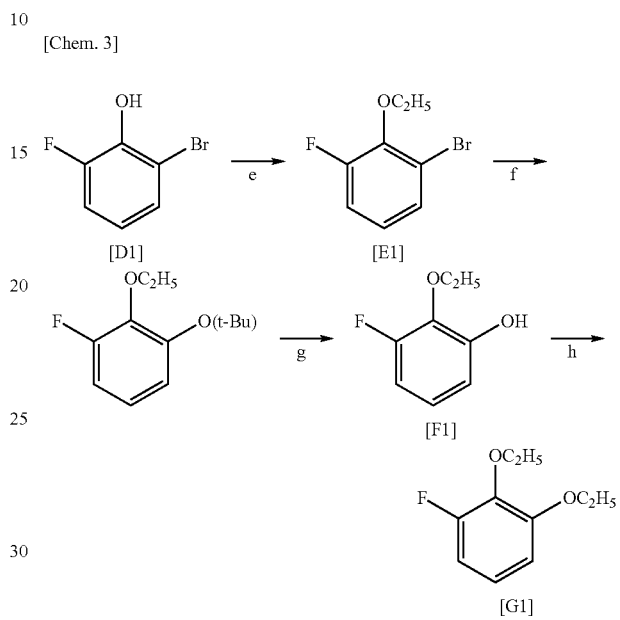

1) Synthesis of 2-fluoro-6-bromo-ethoxybenzene [E1] (Step e)

e: To a 250 ml reactor were added 76.4 (0.4 mol) of 2-fluoro-6-bromophenol [D1], 16 g (0.4 mol) of sodium hydroxide, and 100 ml of ethanol. After cooling to 10° C., 100 ml of an ethanol solution of 48 g (0.44 ml) of bromoethane was slowly added. After the termination of the addition, they were reacted under a reflux temperature for 3 hours and, after the termination of the reaction, dichloromethane was added, followed by extraction. The extraction liquid was washed and dried and the solvent was removed by distillation to obtain 61 g of an oily product [E1]. The process yield was 70%.

2) Synthesis of 2-ethoxy-3-fluorophenol [F1] (Steps f and g)

f: To a 250 ml flask were added 6.6 g (0.28 mol) of a magnesium powder and 10 ml of tetrahydrofuran (THF), and a tetrahydrofuran solution of 55 g (0.25 mol) of [E1] was slowly added dropwise under stirring in a condition where the reaction temperature was kept at 60° C. or lower. After the addition, heat was released and, after the heat release, the reaction mixture was heated to 60° C. to carry out a reaction for 30 minutes. Then, the temperature of the reactor was cooled to 0° C. on an ice bath, and 80 ml of a tetrahydrofuran solution of 48 g (0.25 mol) of tert-butyl perbenzoate was slowly added while the temperature was kept. After the termination of the addition, the mixture was heated to 25° C. to carry out a reaction for 2 hours. The reaction mixture was poured into 1000 ml of a 3% hydrochloric acid solution and ethyl acetate was further added, followed by extraction. The extraction liquid was washed with a sodium carbonate solution and water successively and, after drying, the solvent was removed by distillation to obtain 27 g of a product. The process yield was 50%.

g: Using a 250 ml flask, 21.4 g (0.1 mol) of the above product was dissolved in 100 ml of dichloromethane. Then, 13.4 g (0.1 mol) of $AlCl_3$ was added and the mixture was heated under stirring to a reflux temperature to carry out a reaction for 2 hours. After the termination of cooling, filtration was performed and the low boiling solvent and formed tert-butyl alcohol was removed by distillation under reduced pressure to obtain 14.8 g of an oily product [F1]. The process yield was 95%.

$^1$H-NMR ($CDCl_3$) δ 1.39 (t, J=7.0 Hz, 3H), 4.23 (q, J=7.1 Hz, 2H), 5.87 (s, 1H), 6.62 (ddd, J=1.4, 8.2, 11.1 Hz, 1H), 6.73 (dt, J=1.4, 8.2 Hz, 1H), 6.87 (dt, J=5.9, 8.3 Hz, 1H).

$^{19}$F-NMR ($CDCl_3$) −130.3 ppm (q, 5.8 Hz)

3) Synthesis of 1,2-diethoxy-3-fluorobenzene [G1](Step h)

h: To a 250 ml reactor were added 12.5 (0.08 mol) of 2-ethoxy-3-fluorophenol [F1], 3.2 g (0.08 mol) of sodium hydroxide and 20 ml of ethanol. After cooling to around 10° C., 20 ml of an ethanol solution of 9.6 g (0.088 ml) of bromoethane was slowly added. After the termination of the addition, they were reacted under a reflux temperature for 3 hours and, after the termination of the reaction, dichloromethane was added, followed by extraction. The extraction liquid was washed with water and dried, and the solvent was removed by distillation to obtain 11.0 g of an oily product [G1]. The process yield was 75%.

$^1$H-NMR ($CDCl_3$) δ 1.36 (t, J=7.2 Hz, 3H), 1.43 (t, 7.0 Hz, 3H), 4.06 (q, J=7.0 Hz, 2H), 4.12 (q, J=7.1 Hz, 2H), 6.65-6.72 (m, 2H), 6.92 (m, 1H).

$^{19}$F-NMR ($CDCl_3$)−130.5 ppm (m)

Example 4

Synthesis of 1-methoxy-2-ethoxy-3-fluorobenzene

1-Ethoxy-2-ethoxy-3-fluorobenzene was obtained through synthesis by the same reaction process as in Example 3 except that 31.5 g (0.25 mol) of dimethyl sulfate was used instead of bromoethane in the etherification of the step h. The process yield was 82%.

Example 5

Synthesis of 1,2-diethoxy-3-fluorobenzene [G1]

2-Fluoro-6-iodophenol as a product of Example 2 was hydrolyzed and then subjected to an etherification reaction to obtain 1,2-diethoxy-3-fluorobenzene [G1].

1) Synthesis of 3-fluorocatechol [H]

To a 500 ml flask were added 119 g (0.5 mol) of 2-fluoro-6-iodophenol and 200 ml of a 30% aqueous potassium hydroxide solution and they were reacted under vigorous stirring under a reflux temperature for 8 hours. After the termination of the reaction, the mixture was cooled to ordinary temperature and neutralized with hydrochloric acid to adjust pH between 2 and 3. After filtration, the filtrate was washed with water to obtain 49.9 g of a product [H]. The process yield was 78%.

2) Synthesis of 1,2-diethoxy-3-fluorobenzene [G1]

To a 500 ml flask were added 38.4 (0.3 mol) of 3-fluorocatechol [H], 12 g (0.3 mol) of sodium hydroxide and 100 ml of ethanol. After cooling to around 10° C., 100 ml of an ethanol solution of 76.3 g (0.7 mol) of bromoethane was slowly added. After the termination of the addition, they were reacted under a reflux temperature for 5 hours. After the termination of the reaction, dichloromethane was added, followed by extraction. The extraction liquid was washed with water and dried, and the solvent was removed by distillation to obtain 45.5 g of 1,2-diethoxy-3-fluorobenzene [G1] as an oily product. The process yield was 81%.

While the invention has been described in detail and with reference to specific embodiments thereof, it will be apparent to one skilled in the art that various changes and modifications can be made therein without departing from the spirit and scope thereof.

INDUSTRIAL APPLICABILITY

The 1,2-dialkoxy-3-fluorobenzenes such as 1,2-diethoxy-3-fluorobenzene obtained by the process of the present invention are useful as intermediates of medicaments (see WO 02/085855, WO 2004/078721, WO 2006/018955).

The invention claimed is:

1. A process for producing a 2-fluoro-6-halophenol, which comprises producing a 2-fluoro-6-halophenol using 2-fluorophenol as a starting material, by performing the following steps in the described order: (1) a sulfonation reaction step of introducing a sulfonic acid group into the 4-position with a sulfonating reagent; (2) a halogenation reaction step of introducing a halogen atom into the 6-position using a halogenating reagent; and (3) a step of carrying out an elimination reaction of the sulfonic acid group in an acidic atmosphere to obtain a 2-fluoro-6-halophenol, wherein the halogen atom at the 6-position is a halogen atom other than a fluorine atom.

2. A process for producing a 2-alkoxy-3-fluorophenol, which comprises producing a 2-alkoxy-3-fluorophenol using 2-fluorophenol as a starting material, by performing the following steps in the described order: (1) a sulfonation reaction step of introducing a sulfonic acid group into the 4-position with a sulfonating reagent; (2) a halogenation reaction step of introducing a halogen atom (provided that the halogen atom is a halogen atom other than a fluorine atom) into the 6-position using a halogenating reagent; (3) a step of carrying out an elimination reaction of the sulfonic acid group in an acidic atmosphere to obtain a 2-fluoro-6-halophenol; (4) an etherification reaction step of alkyl-etherifying the hydroxyl group with an alkylating reagent to obtain a 1-alkoxy-2-fluoro-6-halobenzene; and (5) a hydroxylation reaction step of converting the halogen atom into a hydroxyl group by a hydrolysis reaction or a Grignard reaction to obtain a 2-alkoxy-3-fluorophenol, wherein the alkoxy group has 20 or less carbon atoms.

3. The process according to claim 2, wherein the alkoxy group is an ethoxy group.

4. A process for producing a 1,2-dialkoxy-3-fluorobenzene, which comprises producing a 1,2-dialkoxy-3-fluorobenzene using 2-fluorophenol as a starting material, by performing the following steps in the described order: (1) a sulfonation reaction step of introducing a sulfonic acid group into the 4-position with a sulfonating reagent; (2) a halogenation reaction step of introducing a halogen atom (provided that the halogen atom is a halogen atom other than a fluorine atom) into the 6-position using a halogenating reagent; (3) a step of carrying out an elimination reaction of the sulfonic acid group in an acidic atmosphere to obtain a 2-fluoro-6-halophenol; (4) an etherification reaction step of alkyl-etherifying the hydroxyl group with an alkylating reagent to obtain a 1-alkoxy-2-fluoro-6-halobenzene; (5) a hydroxylation reaction step of converting the halogen atom into a hydroxyl group by a hydrolysis reaction or a Grignard reaction to obtain a 2-alkoxy-3-fluorophenol; and (6) an etherification reaction step of alkyl-etherifying the hydroxyl group with an alkylating reagent to obtain a 1,2-dialkoxy-3-fluorobenzene, wherein the two alkoxy groups of the 1,2-dialkoxy-3-fluorobenzene may be the same or different and wherein each of the two alkoxy groups has 20 or less carbon atoms.

5. The process according to claim 4, wherein both of the two alkoxy groups are ethoxy groups.

6. The process according to any of claims 1 to 5, wherein the sulfonating reagent is concentrated sulfuric acid, fuming sulfuric acid, chlorosulfonic acid, or a molecular composite of anhydrous pyridine with sulfur trioxide.

7. The process according to any of claims 1 to 5, wherein the halogenating reagent is $Cl_2$, $Br_2$, $I_2$, or ICl.

8. The process according to claim 1, wherein the 2-fluoro-6-halophenol is produced with yield greater than about 60% based on the 2-fluorophenol starting material.

9. The process according to claim 2, wherein the 2-alkoxy-3-fluorophenol is produced with yield greater than about 20% based on the 2-fluorophenol starting material.

10. The process according to claim 4, wherein the 1,2-dialkoxy-3-fluorobenzene is produced with yield greater than about 40% based on the 2-fluorophenol starting material.

* * * * *